(12) United States Patent
Anand et al.

(10) Patent No.: US 11,638,837 B2
(45) Date of Patent: May 2, 2023

(54) APPARATUS FOR COMBINED LOCALIZATION AND DOSIMETRY IN IMAGE GUIDED RADIATION THERAPY OF THE HEAD AND NECK

(71) Applicant: Mayo Foundation for Medical Education and Research, Rochester, MN (US)

(72) Inventors: Aman Anand, Phoenix, AZ (US); Martin Bues, Scottsdale, AZ (US); Samir H. Patel, Scottsdale, AZ (US); Tania Jain, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 5 days.

(21) Appl. No.: 16/604,718

(22) PCT Filed: Apr. 16, 2018

(86) PCT No.: PCT/US2018/027717
§ 371 (c)(1),
(2) Date: Oct. 11, 2019

(87) PCT Pub. No.: WO2018/191737
PCT Pub. Date: Oct. 18, 2018

(65) Prior Publication Data
US 2020/0376297 A1  Dec. 3, 2020

Related U.S. Application Data

(60) Provisional application No. 62/485,706, filed on Apr. 14, 2017.

(51) Int. Cl.
*A61N 5/00* (2006.01)
*A61N 5/10* (2006.01)

(52) U.S. Cl.
CPC ........ *A61N 5/1049* (2013.01); *A61N 5/1031* (2013.01); *A61N 2005/1051* (2013.01); *A61N 2005/1097* (2013.01)

(58) Field of Classification Search
CPC ....... A61B 6/04; A61B 6/0407; A61B 6/0485; A61B 6/0492; A61B 6/08; A61B 6/14;
(Continued)

(56) References Cited

U.S. PATENT DOCUMENTS 1,733,507 A * 10/1929 McCollum ........... A61C 11/022
433/67
3,419,004 A * 12/1968 Berman ............ A61M 16/0488
128/207.14
(Continued)

FOREIGN PATENT DOCUMENTS

KR          101478816 B1      1/2015

OTHER PUBLICATIONS https://www.thefreedictionary.com/telescopic (Year: 2016).*
International Search Report and Written Opinion from parent PCT/US2018/027717, dated Sep. 21, 2018, 16 pages.

*Primary Examiner* — Dani Fox
(74) *Attorney, Agent, or Firm* — Quarles & Brady LLP

(57) ABSTRACT

Apparatus for improving image guidance in radiation therapy applications are described. In one aspect, a patient support with integrated radiopaque markers is described. In another aspect, a bite block with integrated sensors, radiopaque markers, or both, is described. The integrated sensors may include a radiation detector, a pH sensor, or both. Radiation detectors that may be used include a dosimeter. As an example, the dosimeter may include a film dosimeter, an ion chamber dosimeter, a diode dosimeter, or other suitable dosimeters and combinations thereof.

16 Claims, 5 Drawing Sheets

(58) Field of Classification Search
CPC ......... A61B 6/145; A61B 6/42; A61B 6/4208; A61B 6/425; A61B 6/50; A61B 6/501; A61B 6/5294; A61B 6/54; A61B 6/547; A61B 6/58; A61B 6/582–584; A61B 13/00; A61B 17/24; A61B 34/20; A61B 50/20; A61B 90/10; A61B 90/11; A61B 90/14; A61B 90/16; A61B 90/36; A61B 90/361; A61B 90/37; A61B 90/39; A61B 2017/0046; A61B 2017/00477; A61B 2017/00725; A61B 2017/00814; A61B 2017/0092; A61B 2017/00946; A61B 2017/00955; A61B 2017/00991; A61B 2018/00982; A61B 2034/2046; A61B 2034/2055; A61B 2034/2065; A61B 2090/0807; A61B 2090/0811; A61B 2090/101; A61B 2090/363; A61B 2090/364; A61B 2090/376; A61B 2090/3904; A61B 2090/392; A61B 2090/3966; A61B 2090/3983; A61B 2090/3991; A61B 2218/001; A61B 2218/002; A61B 2560/0223; A61B 2560/0233; A61B 2560/0238; A61B 2560/04; A61B 2560/0406; A61B 2560/0443; A61B 2560/0462; A61B 2560/06; A61B 2562/02; A61B 2562/0233; A61B 2562/16; A61B 2562/164; A61B 2562/17; A61B 2576/02; A61B 2576/026; A61B 1/24; A61B 2017/00557; A61N 5/10; A61N 5/1048; A61N 5/1049; A61N 5/1071; A61N 5/1075; A61N 5/1092; A61N 2005/1056; A61N 2005/1061; A61N 2005/1072; A61N 2005/1076; A61N 2005/0626; A61N 2005/0627; A61N 2005/0628; A61N 2005/0635; G01N 21/80; G01N 23/02; G01N 23/04; G01N 23/06; G01N 23/083; G01N 2223/30; G01N 2223/303; G01N 2223/3035; G01N 2223/321; G01N 2223/40; G01N 2223/612; G01N 2223/6123; G01N 2223/6126; G01T 1/00; G01T 1/02; G01T 1/023; G01T 1/026; G01T 1/04; G01T 1/08; G01T 1/14; G01T 1/16; G01T 1/20188; G01T 1/24; G01T 1/244; G01T 1/29; G01T 7/00; G01T 7/005; G21K 5/00; G21K 5/08; A61C 8/0001; A61C 17/02; A61C 17/227; A61C 5/90; A61K 6/90; A61G 13/12; A61G 13/1205; A61G 13/121; A61G 13/126; A61G 13/1265; A61G 15/10; A61G 15/12; A61G 15/125

See application file for complete search history.

(56) References Cited

U.S. PATENT DOCUMENTS

| | | | | |
|---|---|---|---|---|
| 3,774,616 | A * | 11/1973 | White | A61M 16/0488 128/200.26 |
| 5,269,175 | A * | 12/1993 | Chmiel | G01N 33/2888 324/675 |
| 6,245,057 | B1 * | 6/2001 | Sieben | A61B 5/145 424/422 |
| 9,079,024 | B2 * | 7/2015 | Koller | G21F 3/00 |
| 9,504,537 | B2 * | 11/2016 | Johnson | A61N 5/10 |
| 9,757,065 | B1 * | 9/2017 | Suri | A46B 15/0006 |
| 2004/0033468 | A1 * | 2/2004 | Fischer | A61C 5/90 433/140 |
| 2006/0065273 | A1 * | 3/2006 | Lewis | A61B 46/00 128/849 |
| 2010/0294283 | A1 * | 11/2010 | Li | A61F 5/566 128/848 |
| 2012/0043475 | A1 * | 2/2012 | Ahn | A61N 5/1049 250/453.11 |
| 2012/0434475 | | 2/2012 | Ahn | |
| 2012/0167897 | A1 * | 7/2012 | Bettega | A61B 6/107 128/859 |
| 2015/0037749 | A1 * | 2/2015 | Levine | A61B 5/4277 433/27 |
| 2016/0015321 | A1 * | 1/2016 | Hashemian | G16H 10/40 600/349 |
| 2017/0197052 | A1 * | 7/2017 | Tylka | A61M 16/0497 |
| 2017/0304024 | A1 * | 10/2017 | Nobrega | A61C 7/08 |
| 2018/0000563 | A1 * | 1/2018 | Shanjani | A61B 5/682 |

* cited by examiner

APPARATUS FOR COMBINED LOCALIZATION AND DOSIMETRY IN IMAGE GUIDED RADIATION THERAPY OF THE HEAD AND NECK

CROSS-REFERENCE TO RELATED APPLICATIONS

This application is a 371 U.S. National Phase application of PCT/US2018/027717, filed Apr. 16, 2018, which claims the benefit of U.S. Provisional Patent Application Ser. No. 62/485,706, filed on Apr. 14, 2017, and entitled "Patient Immobilization Support with Integrated Radio-Opaque Markers and Multi-Functional Bite Block with Integrated Dosimeter and pH Sensor."

BACKGROUND

Protecting normal tissues abutting tumor volumes in a typical treatment for head and neck cancers with ionizing radiations (x-rays and particles such as protons, carbon ions, and so on) is still an unmet need in radiotherapy clinics. Often times when treating disease of the oral cavity, the floor of the cavity and the tongue remain susceptible to large amounts of extraneous doses of ionizing radiations. In order to avoid or to mitigate dose spills into healthy tissues such as tongue, aids of tongue depressants often termed bite blocks or stents are used. Bite blocks are generally made out of plastic or foam and can come in different shapes. In use, the bite block is positioned between openings in a thermoplastic mask, and the patient is asked to bite upon the bite block in order to maintain the structural integrity and position of the lower jaw bone, around which then an immobilization mask then gets prepared.

The challenge with such a setup is once the bite block is positioned within the mask and inside the oral cavity of the patient, there are no markers to provide unique spatial localization information on the bite block, nor is there visual access to assess the positioning of the bites block. Additionally, day-to-day variability in the actual positioning of the tongue can be difficult to monitor and, consequentially, the treatment planning predicted dose to tongue and oral cavity remains more speculative in nature than quantitative.

Because bite blocks are nearly transparent to kV x-rays (e.g., those used in CT simulations), they are harder to see on routine clinical x-ray imaging. As a result, the bite block cannot be reliably positioned via image guidance in their original positions, and hence there remains large excursions in their actual positioning within the patient's mouth during treatment.

Image Guided Radiotherapy ("IGRT") coupled with a sophisticated immobilization solution has become a must-have requirement for any clinic treating cancers of the brain, head, and neck regions with intensity modulated ionization radiation photon or particle beams (IMRT/IMPT). While IGRT has several dosimetric advantages in treating patients with IMRT/IMPT plans, there are also significant risks of geometric misses of the target if either the patient or the image guidance system fails to position the target in the original position for which the treatment plan was generated. Because the risks of geometric misses are scored heavily in safety protocols of a clinic, the processes of setting up patients every single day of their treatments end up becoming an exhaustive, labor intensive, resource heavy exercise for these treatments.

While setting up a patient for their radiation treatments is a multi-step process and varies from clinic to clinic, the first step generally begins with preparing the immobilization devices in the treatment room to mimic the original position during the simulation scans. One of the device that is routinely used to position the base of a patient's skull on the table is a head rest, which comes in various forms and shapes. Depending upon the immobilization patient support device, these cushions can be utilized for supporting both the head and the neck of the patient. Reproducibility of positioning the cushion over the table top, in addition to lack of confidence in positioning the head over the cushion, remains a regular complaint of radiation therapists involved with these procedures. Often times, neither the cushion nor the head are positioned exactly the same way with respect to the table top as they were during the treatment planning scans. Common complaints in these clinics include: the sliding of the cushion on the table tops, non-indexability of the cushions, neck rotations, and incorrect pivotal positions of the neck.

Even though IGRT is utilized to position and align patients on the table for their treatments, there are no indicative parameters within conventional patient support cushions that describe their location on any single day of the treatment. In addition, due to the pivotal nature of the neck, there are often issues related to the positioning of the neck on top of these head rest cushions. These instances often require physically shifting patients in superior/inferior directions multiple times with iterative x-ray imaging until the right neck position falls upon the correct cushion location. Both the neck and the cushion position are then adjusted on top of the table top. This whole process can often take upwards of 15-20 minutes per patient every single day, and can add to clinical burden and fatigue. In addition, due to the iterative nature of IGRT, patients receive extraneous radiation (albeit low) doses from x-rays utilized during IGRT, which could be reduced if there were options of better indexing of these devices.

SUMMARY OF THE DISCLOSURE

The present disclosure addresses the aforementioned drawbacks by providing a bite block that includes a mouthpiece, a tongue depressor, and a sheath coupling the mouthpiece to the tongue depressor. The mouthpiece has formed therein a channel that is shaped to be retained by a patient's teeth when positioned in an oral cavity of the patient. A port extends through the mouthpiece from a forward surface of the mouthpiece to a rear surface of the mouthpiece. The sheath extends from a proximal end at the rear surface of the mouthpiece to a distal end at the tongue depressor to couple the mouthpiece to the tongue depressor. At least one radiopaque marker is coupled to the tongue depressor, and a pH sensor is also coupled to the tongue depressor.

It is another aspect of the present disclosure to provide a patient support that includes a cushion and a radiopaque assembly coupled to an exterior surface of the cushion. The radiopaque assembly includes a radiolucent plate and a plurality of radiopaque indicia arranged on the radiolucent plate in an arrangement that indicates spatial location information.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full

DETAILED DESCRIPTION

Described here are apparatus for improving image guidance in radiation therapy applications. In one aspect, the present disclosure describes a patient support with integrated radiopaque markers. The patient support may be in some implementations a patient immobilization support. As one example, the patient immobilization support may be a pillow or other supportive cushion. In another aspect, the present disclosure describes a bite block with integrated sensors, radiopaque markers, or both. In some implementations, the integrated sensors may include a radiation detector, a pH sensor, or both. Radiation detectors that may be used include a dosimeter. As an example, the dosimeter may include a film dosimeter, an ion chamber dosimeter, a diode dosimeter, scintillators, or other suitable dosimeters and combinations thereof.

Figure 1:
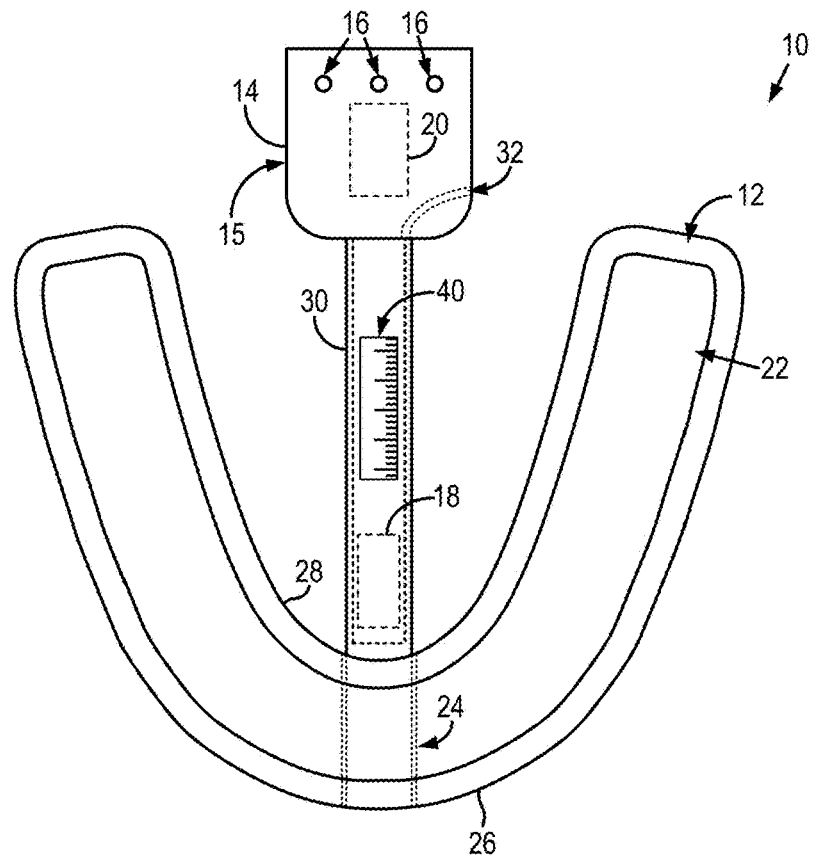
FIG. 1 is an example of a bite block with integrated radiopaque markers, dosimeter, and pH sensor, according to some embodiments of the present disclosure.
Figure 2:
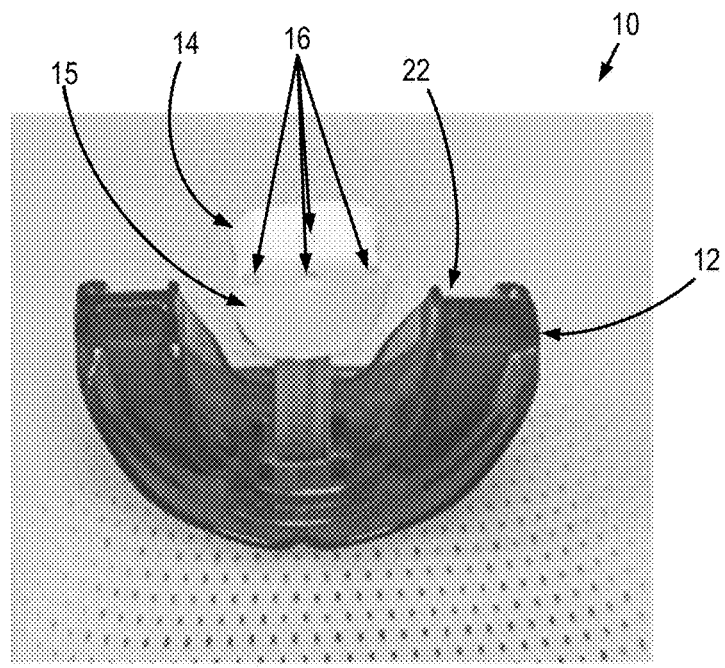
FIG. 2 is another view of the bite block of FIG. 1.

Referring now to FIGS. 1 and 2, an example of a bite block 10 having embedded radiopaque markers and sensors is shown. The bite block 10 generally includes a mouthpiece 12 and a tongue depressor 14. One or more radiopaque markers 16 are embedded or otherwise arranged on the bite block 10. The bite block 10 may also include one or more dosimeters 18 for measuring radiation dose, one or more physiological sensors 20 for measuring physiological data, or both.

As one example, the radiopaque markers 16 may be embedded in or otherwise coupled to the tongue depressor 14. One or more radiopaque markers 16 may also be embedded in or coupled to other components of the bite block 10, including the mouthpiece 12. The radiopaque markers 16 can include radiopaque spheres, beads, dots, wires, or other markers. In general, the radiopaque markers 16 are composed of one or more radiopaque materials, such as suitable metals or metal alloys.

The mouthpiece 12 is configured to be received in an oral cavity of a patient, and has a channel 22 that is retained by the patient's teeth when the bite block 10 is received in the oral cavity of the patient. The mouthpiece 12 can be composed of a suitable flexible material, such as a molded plastic, foam, or so on, in order to comfortably fit the patient's teeth irrespective of the patient's jaw size. In some embodiments, ridges can be formed in the channel 22. The ridges are shaped to receive a putty, which can further stabilize the teeth position.

A port 24 is formed in the mouthpiece 12 and extends from a front surface 26 of the mouthpiece 12 to a rear surface 28 of the mouthpiece 12. A sheath 30 extends from the mouthpiece 12 to the tongue depressor 14 and couples the mouthpiece 12 to the tongue depressor 14. In some embodiments, the sheath 30 is a telescoping sheath (as indicated by dashed lines 31 in FIGS. 1 and 3) that is operable to extend the tongue depressor 14 to different depths relative to the mouthpiece 12. This feature allows for a patient specific configuration of the bite block 10.

The sheath 30 may extend through the port 24 from the rear surface 28 of the mouthpiece 12 to the front surface 26 of the mouthpiece 12. In some embodiments, the sheath 30 generally includes a tubular structure having a lumen that extends from the mouthpiece 12 to the tongue depressor 14. For instance, the lumen may connect the port 24 to an internal cavity formed in the tongue depressor 14. The sheath 30 allows for the insertion of one or more dosimeters 18 to measure radiation dose during treatment, one or more sensors 20 to measure physiological or other data, or combinations thereof.

The dosimeter 18 may be positioned in the sheath 30 during treatment, or can be provided to an interior cavity formed in the tongue depressor 14 via the sheath 30. As one example, the dosimeter 18 can be an ion chamber dosimeter. As another example, the dosimeter 18 can be a diode dosimeter. As still another example, the dosimeter 18 can be a film dosimeter. In some embodiments, one or more slits can be formed in the tongue depressor 14 to receive a film dosimeter. Such film dosimeters may include Gafchromic film, or other suitable radiochromic film. In still other embodiments, the dosimeter 18 can be a scintillator dosimeter.

One or more sensors 20 can be embedded in, coupled to, or otherwise provided to the tongue depressor 14. For instance, a sensor 20 can be embedded in the tongue depressor 14, coupled to an exterior surface of the tongue depressor 14, arranged in an interior cavity formed in the tongue depressor 14, or so on. In some embodiments, the sensor 20 can be provided to an interior cavity formed in the tongue depressor 14 by way of the sheath 30. In such instances, the sensor 20 may be a removable sensor 20, such that the sensor 20 can be removed from or placed into the interior cavity of the tongue depressor 14 during treatment or while the patient is otherwise immobilized in preparation for treatment.

In one embodiment, the sensor 20 is a pH sensor that measures pH data from the oral cavity of the patient. For instance, the pH sensor can monitor the pH of the patient's saliva during treatment and over the course of treatment. In other embodiments, the sensor 20 can measure other physiological data, including other electrochemistry data. As one example, the pH sensor can include pHFET (pH ion selective field effect transistors) as the sensing element. In some implementations, the pH sensor can include a strip of pHFET. The strip may have a thickness on the order of microns. The pH sensor can in some configurations detect or otherwise measure the mobility of molar hydronium and hydroxonium ions. As one example, the pH sensor can be manufactured using nanolithography techniques. In such instances, the pH sensor can be manufactured to include MOSFET circuitry that can encase sensitive electrodes, which can then be integrated within the bite block 10.

The tongue depressor 14 can in some embodiments be coated with edible flavors. In some configurations, a port 32 can be formed in the tongue depressor 14. For instance, the port 32 can extend from the sheath 30 to an exterior surface of the tongue depressor 14 such that a fluid can be delivered from the sheath 30, through the port 32, and out of the tongue depressor 14. As one non-limiting example, the port 32 can be a medicinal port for releasing pain management medicines or other pharmacological agents during the treatment.

Figure 3:
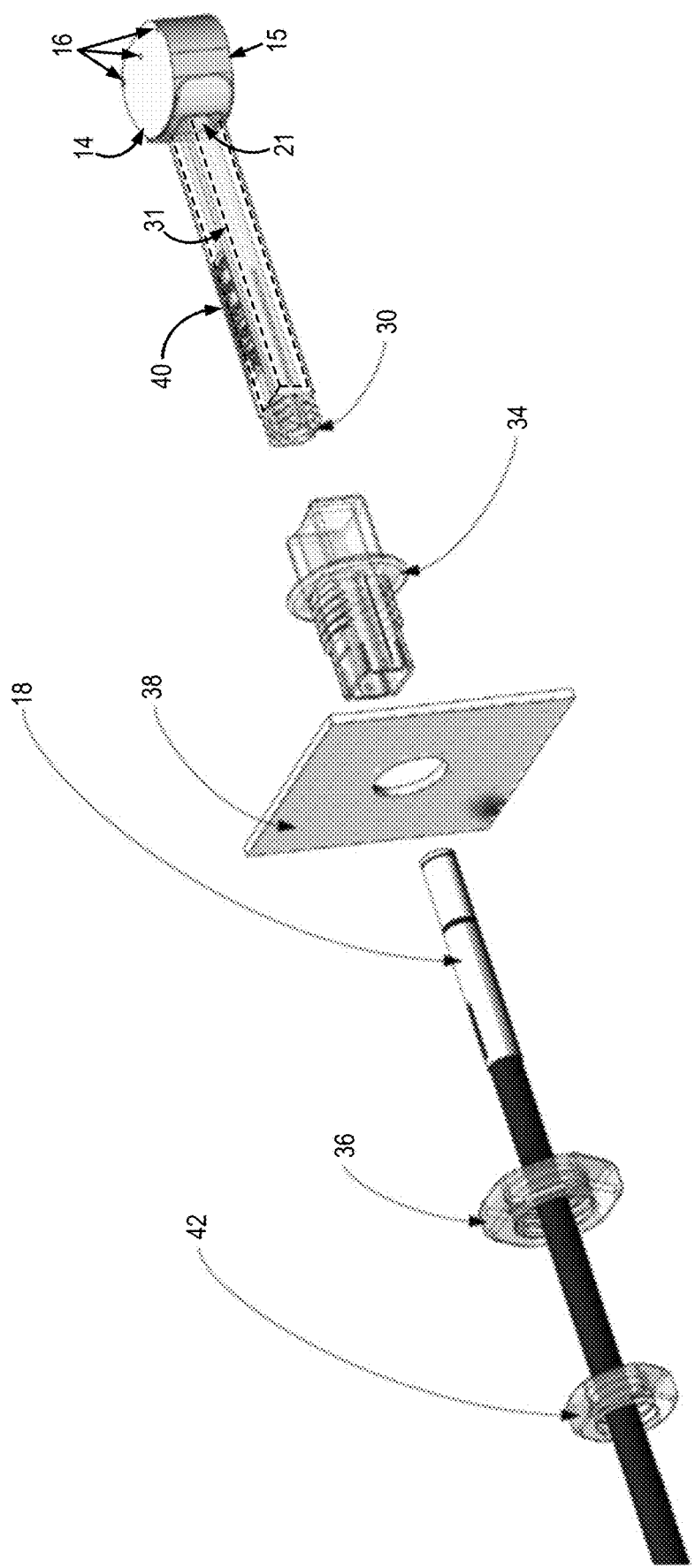
FIG. 3 is an example of some of the components of the bite block of FIG. 1, including those for securing the bite block assembly to a face mask, such as a patient immobilization face mask.
Figure 4:
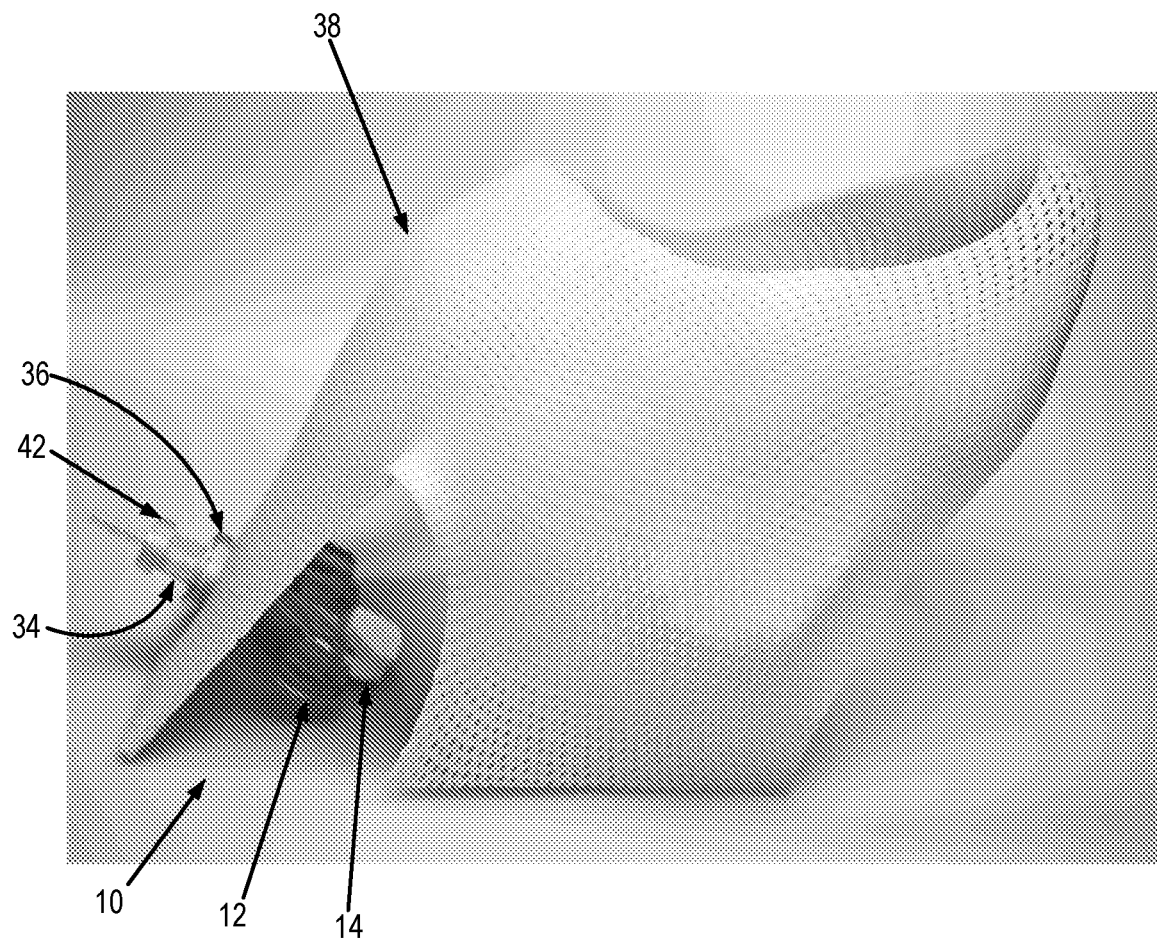
FIG. 4 shows an example of the bite block of FIG. 1 being secured to a patient immobilization face mask.

Referring now to FIG. 3, an exploded view of some components of the bite block 10 is shown. In this example, a face mask attachment guide 34 in conjunction with a nut 36 allows for a stable and reproducible attachment of the bite block 10 to a face mask 38. As noted above, the sheath 30 may be a telescoping sheath (as indicated by dashed lines 31 in FIGS. 1 and 3). In these instances, a distance scale 40 can be provided on an exterior surface of the sheath 30 to provide a recordable and reproducible tongue depressor 14 insertion. The face mask attachment guide 34 and the sheath 30 allow for the insertion of a dosimeter 18 (e.g., a diode dosimeter) into the tongue depressor 14. The dosimeter 18 can be held in place by a cable crimp nut 42. Radiopaque markers 16 can be affixed or otherwise coupled to the tongue depressor 14 and to the face mask attachment guide 34 to allow for the positioning of the bite block 10 under x-ray radiography (e.g., planar x-rays and x-ray tomography). FIG. 4 shows an example of the bite block 10 affixed to a face mask 38 using the face mask attachment guide 36, nut 36, and cable crimp nut 42.

Figure 5:
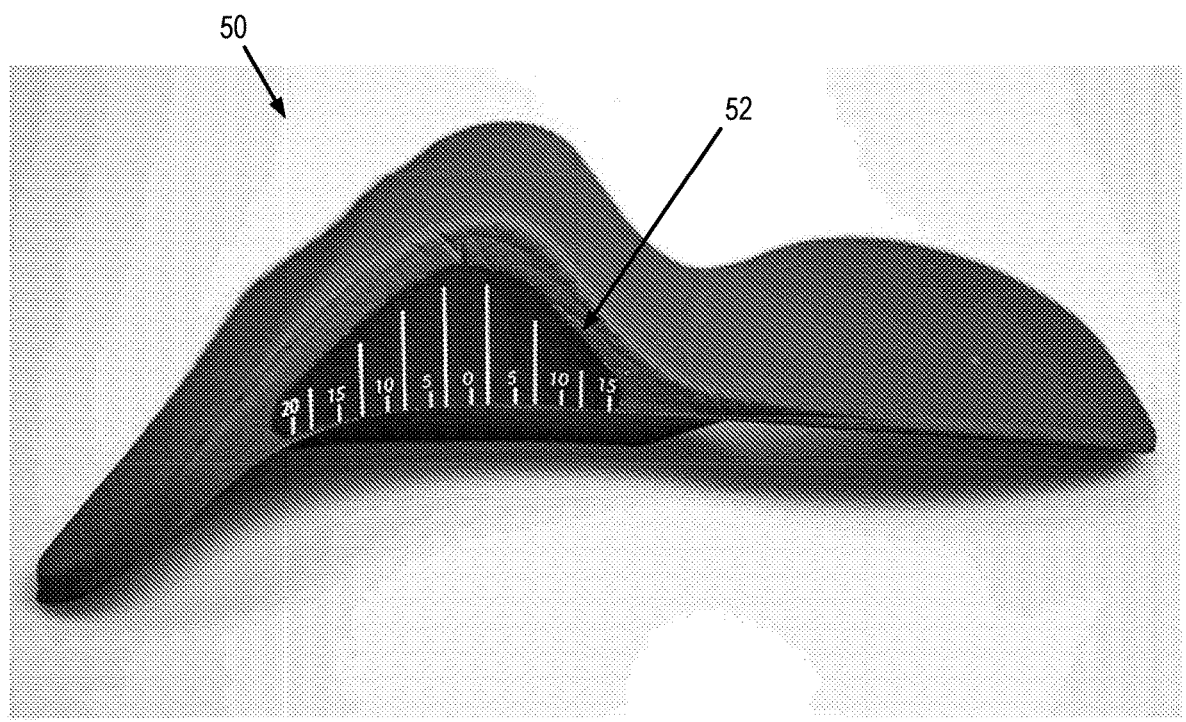
FIG. 5 is an example of a patient support with integrated radiopaque markers for repeatedly and reliably aligning the patient support during a radiation treatment.
Figure 6:
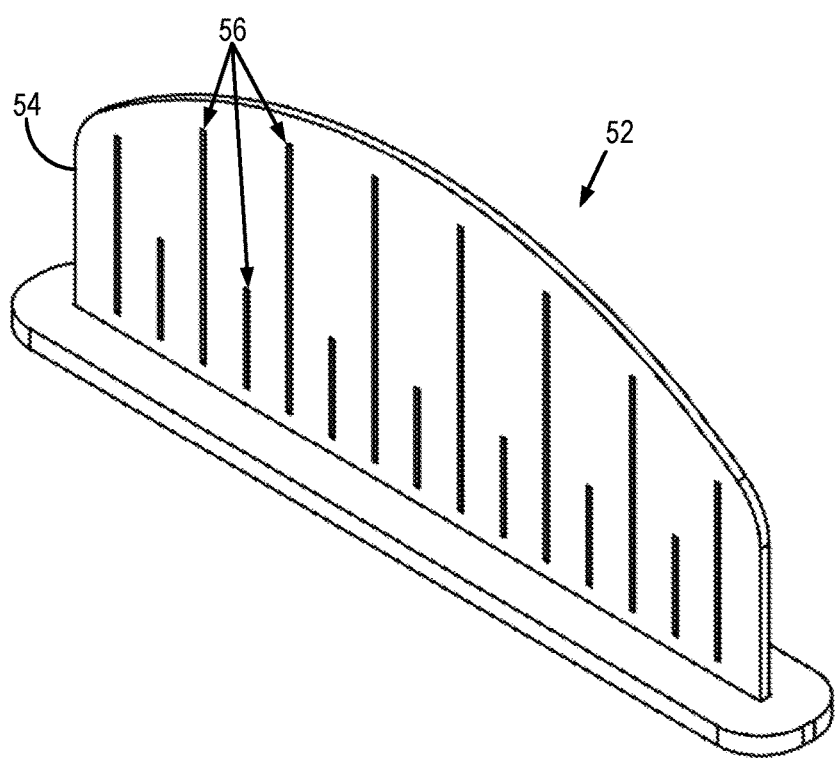
FIG. 6 is an example of a radiopaque marker assembly for use with the patient support shown in FIG. 5.

Referring now to FIG. 5, an example of a patient support 50 with an integrated radiopaque marker assembly 52 is shown. FIG. 6 shows an example of a radiopaque marker assembly 52.

The patient support 50 can be a pillow, cushion, or other suitable patient support. As an example, the patient support 50 can be a head cushion used for support the head and neck of a patient during a radiation treatment procedure.

The radiopaque marker assembly 52 can include a plate 54 having formed thereon a plurality of radiopaque indicia 56 that enable repeatable and reliable positioned of the patient support 50 to a fixed reference position. For instance, the fixed reference position can be a fixed reference position on the treatment table top. IGRT can then be utilized to post the head tilt/neck position on top of the patient support 50 for efficient, safe, and reproducible setups. In some embodiments, additional radiopaque markers can be embedded in or otherwise coupled to the patient support 50.

The radiopaque indicia 56 can include, for instance, linear elements composed of a radiopaque material. In some embodiments, the radiopaque indicia 56 are radiopaque wires that are embedded in or otherwise coupled to the plate 54. The plate 54 may be a rigid plate composed of a hard, radiolucent material. The plate 54 may be composed of plastic. The plate 54 is affixed to or otherwise coupled to the patient support 50.

In some embodiments, the radiopaque indicia 56 can be differently colored to facilitate visual alignment of the patient support 50 with the fixed reference point. By matching a fixed color marker to the reference point (e.g., table top) and then imaging the patient on top of the patient support 50, the location of critical structures that need to be reproduced can be quantitatively assessed.

The radiopaque indicia 56 can be arranged in a pattern, such as a scale, which may be a distance scale. In such implementations, the radiopaque indicia 56 can be spaced apart by well-defined distances, such that the radiopaque indicia 56 can be relied upon to repeatedly and reliably position the patient support 50 relative to a reference point.

As one non-limiting example, the patient support 50 can be a head cushion. The radiopaque indicia 56 in the radiopaque marker assembly 52 can include vertical half centimeter marks affixed to the exterior of the cushion, thereby allowing for positioning of the patient's appropriate cervical vertebra at the center of the cushion. Radiopaque markers in the interior of the head cushion are in one-to-one correspondence with the markers affixed to the exterior of the cushion and allow for the x-ray radiographic (planar x-rays as well as x-ray tomography) verification of the positioning of the cervical vertebra relative to the cushion.

Figure 7:
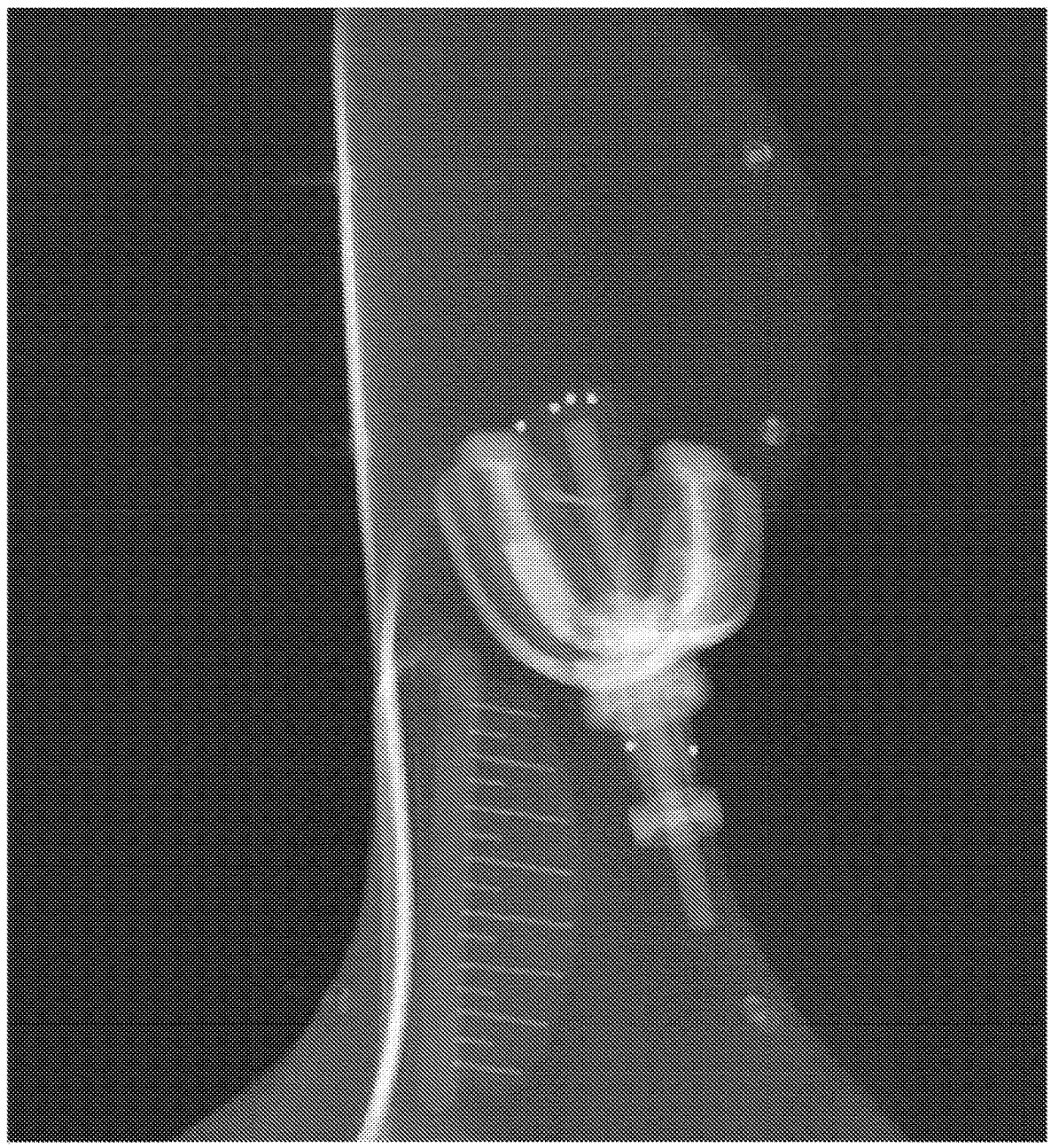
FIG. 7 is a planar x-ray radiograph of bite block and patient support described in the present disclosure. The bite block is shown in the center of the image. Radiopaque markers appear as bright dots in the x-ray radiograph. The head cushion is shown in the lower part of the image. Radiopaque wires appear as bright straight lines of varying lengths.

FIG. 7 is a planar x-ray radiograph of bite block and patient support described in the present disclosure. The bite block is shown in the center of the image. Radiopaque markers appear as bright dots in the x-ray radiograph. The head cushion is shown in the lower part of the image. Radiopaque wires appear as bright straight lines of varying lengths.

The present disclosure has described one or more preferred embodiments, and it should be appreciated that many equivalents, alternatives, variations, and modifications, aside from those expressly stated, are possible and within the scope of the invention.

The invention claimed is:

1. A bite block, comprising:
   a mouthpiece having formed therein a channel that is shaped to be retained by a patient's teeth when positioned in an oral cavity of the patient;
   a port extending through the mouthpiece from a forward surface of the mouthpiece to a rear surface of the mouthpiece;
   a tongue depressor;
   a sheath extending from a proximal end at the rear surface of the mouthpiece to a distal end at the tongue depressor to couple the mouthpiece to the tongue depressor, wherein the sheath is a telescoping sheath that is operable to be adjusted to change a depth of the tongue depressor relative to the rear surface of the mouthpiece and the sheath further comprises a distance scale coupled to the telescoping sheath, wherein the distance scale indicates the depth of the tongue depressor as the telescoping sheath is adjusted;
   at least one radiopaque marker coupled to the tongue depressor; and
   a pH sensor coupled to the tongue depressor.

2. The bite block as recited in claim 1, wherein the tongue depressor comprises an internal cavity and the pH sensor is arranged within the internal cavity.

3. The bite block as recited in claim 1, further comprising at least one dosimeter coupled to at least one of the sheath or the tongue depressor.

4. The bite block as recited in claim 3, wherein the tongue depressor comprises an internal cavity and the at least one dosimeter is removably arranged in the internal cavity via the sheath.

5. The bite block as recited in claim 3, wherein the at least one dosimeter comprises at least one of a diode dosimeter, an ion chamber dosimeter, or a film dosimeter.

6. The bite block as recited in claim 3, wherein the at least one dosimeter is arranged in the sheath.

7. The bite block as recited in claim 1, further comprising at least one additional radiopaque marker coupled to at least one of the mouthpiece or the sheath.

8. The bite block as recited in claim 1, wherein the at least one radiopaque marker comprises a plurality of radiopaque markers arranged in a pattern that provides for localization of the tongue depressor in an x-ray image that depicts the tongue depressor.

9. The bite block as recited in claim 1, wherein the mouthpiece is composed of a flexible material.

10. The bite block as recited in claim 9, wherein the flexible material is a flexible plastic.

11. The bite block as recited in claim 1, further comprising a plurality of ridges formed in the channel in order to provide a surface for receiving a putty.

12. The bite block as recited in claim 1, wherein the tongue depressor is coated with a flavored coating.

13. The bite block as recited in claim 1, further comprising a port formed in the tongue depressor and extending to an exterior surface of the tongue depressor to provide for fluid communication through the exterior surface of the tongue depressor.

14. The bite block as recited in claim 1, wherein the pH sensor comprises pH ion selective field effect transistors.

15. The bite block as recited in claim 1, wherein the at least one radiopaque marker comprises at least one of a radiopaque sphere, bead, or wire.

16. A patient support, comprising:
a cushion; and
a radiopaque assembly coupled to an exterior surface of the cushion, wherein the radiopaque assembly comprises:
a radiolucent plate;
a plurality of radiopaque indicia arranged on the radiolucent plate in an arrangement that indicates spatial location information, wherein the plurality of radiopaque indicia comprises a plurality of spaced apart linear radiopaque markers and wherein some of the plurality of spaced apart linear radiopaque markers are longer than others of the plurality of spaced apart linear radiopaque markers so as to indicate delineations on a distance scale; and
an internal radiopaque assembly arranged in an interior portion of the cushion, wherein the internal radiopaque assembly comprises a plurality of radiopaque markers that are arranged relative to the plurality of radiopaque indicia in a known configuration in order to relate the spatial position of the plurality of radiopaque markers with the spatial position of the radiopaque indicia.

* * * * *